United States Patent [19]

Pehu et al.

[11] Patent Number: 5,576,202
[45] Date of Patent: Nov. 19, 1996

[54] VIRUS-RESISTANT TRANSGENIC PLANTS

[75] Inventors: Eija Pehu; Tuula Pehu; Tuula Maki-Valkama; Jari Valkonen; Kimmo Koivu; Kirsi Lehto, all of Helsinki, Finland

[73] Assignee: Helsinki University Licensing, Ltd., Helsinki, Finland

[21] Appl. No.: 246,123

[22] Filed: May 19, 1994

[51] Int. Cl.⁶ .......................... C12N 15/00; C12N 5/14; A01H 1/04
[52] U.S. Cl. .................... 435/172.3; 435/240.4; 435/240.51; 800/205; 800/DIG. 42
[58] Field of Search .......................... 800/205, DIG. 42; 435/172.3, 240.4, 240.51

[56] References Cited

PUBLICATIONS

Kanrewshi et al (1990) Bio/Technology 8:750–754.
Anderson et al., "A defective replicase gene induces resistance to cucumber mosaic virus in transgenic tobacco plants," *Proc. Natl. Acad. Sci. USA*, 89:8759–8763 (Sep. 1992).
Audy et al., "Replicase–Mediated Resistance to Potato Virus Y in Transgenic Tobacco Plants," *Mol. Plant–Microbe Interac.*, 7(1):15–22 (1994).
Ausubel et al ed., "Polymerase Chain Reaction," section 15 of *Current Protocols in Molecular Biology* (Current Protocols) (1989).
Barnett et al., "Potyviridae, a proposed family of plant viruses," *Arch. Virology*, 118:139–141 (1991).
Brantley and Hunt, "The N–terminal protein of the polyprotein encoded by the potyvirus tobacco vein mottling virus is a RNA–binding protein," *J. Gen. Virol.*, 74:1157–1162 (1993).
Braun and Hemenway, "Expression of Amino–Terminal Portions or Full–Length Viral Replicase Genes in Transgenic Plants Confers Resistance to Potato Virus X Infection," *Plant Cell*, 4:735–744 (Jun. 1992).
Carr et al., "Resistance to Tobacco Mosaic Virus Induced by the 54–kDa Gene Sequence Requires Expression of the 54–kDa Protein," *Mol. Plant–Microbe Interac.*, 5(5):397–404 (1992).
Dellaporta et al., "A plant DNA Minipreparation: Version II," *Plant Mol. Biol. Rep.*, 1(4):19–21 (1983).
Dougherty and Carrington, "Expression and Function of Potyviral Gene Products," *Annu. Rev. Phytopathol.*, 26:123–143 (1988).
Edwards et al., "A simple and rapid method for the preparation of plant genomic DNA for PCR analysis," *Nucl. Acids Res.*, 19(6):1349 (1991).
Gibson et al., "Resistance to potato virus Y and potato virus X in *Solanum brevidens*," *Ann. appl. Biol.*, 116:151–156 (1990).
Golemboski et al., "Plants transformed with a tobacco mosaic virus nonstructural gene sequence are resistant to the virus," *Proc. Natl. Acad. Sci. USA*, 87:6311–6315 (Aug. 1990).
Herskowitz, "Functional inactivation of genes by dominant negative mutations," *Nature*, 329:219–222 (Sep. 17, 1987).

Hull and Davies, "Approaches to Nonconventional Control of Plant Virus Diseases," *Crit. Rev. Plant. Sci.*, 11(1):17–33 (1992).
Longstaff et al., "Extreme resistance to potato virus X infection in plants expressing a modified component of the putative viral replicase," *EMBO J.*, 12(2):379–386 (1993).
Maiti et al., "Plants that express a potyvirus proteinase gene are resistant to virus infection," *Proc. Natl. Acad. Sci. USA*, 90:6110–6114 (Jul. 1993).
Malyshenko et al., "Reduction of tobacco mosaic virus accumulation in transgenic plants producing non–functional viral transport proteins," *J. Gen. Virol.*, 74:1149–1156 (1993).
McDonnell et al., "A Simplified Method for the Detection of Neomycin Phosphotransferase II Activity in Transformed Plant Tissues," *Plant Mol. Biol. Rep.*, 9(4):380–386 (1987).
Murashige and Skog, "A Revised Medium for Rapid Growth and Bio Assays with Tobacco Tissue Cultures," *Physiologia Plantarum*, 15:473–497 (1962).
Riechmann et al., "Highlights and prospects of potyvirus molecular biology," *J. Gen. Virol.*, 73:1–16 (1992).
Robaglia et al., "Nucleotide Sequence of Potato Virus Y (N strain) Genomic RNA," *J. Gen. Virol.*, 70:935–947 (1989).
Sambrook et al., sections 7.3–7.84 and 8.3–8.82 in *Molecular Cloning: A Laboratory Manual* (1989).
Sanford and Johnston, "The Concept of Parasite–Derived Resistance–Deriving Resistance Genes from the Parasite's Own Genome," *J. Theor. Biol.*, 113:395–405 (1985).
Sanger et al., "DNA sequencing with chain–terminating inhibitors," *Proc. Natl. Acad. Sci. USA*, 74(12):5463–5467 (Dec. 1977).
Thornbury et al., "Comparative Sequence of the Helper Component (HC) Region of Potato Virus Y and a HC–Defective Strain, Potato Virus C," *Virology*, 178:573–578 (1990).
Van Haute et al., "Intergenetic transfer and exchange recombination of restriction fragments cloned in pBR322: a novel strategy for the reversed genetics of the Ti plasmids of *Agrobacterium tumefaciens*," *EMBO J.*, 2(3):411–417 (1983).
Van Larebeke et al., "Large plasmid in *Agrobacterium tumefaciens* essential for the crow gall–inducing ability," *Nature*, 252:169–170 (Nov. 8, 1974).
Vardi et al., "Plants transformed with a cistron of a potato virus Y protease (NIa) are resistant to virus infection," *Proc. Natl. Acad. Sci. USA*, 90:7513–7517 (Aug. 1993).
Verchot et al., "The 35–kDa Protein from the N–terminus of the Potyviral Polyprotein Functions as a Third Virus–Encoded Proteinase," *Virology*, 185:527–535 (1991).
Zambryski et al., "Ti plasmid vector for the introduction of DNA into plant cells without alteration of their normal regeneration capacity," *EMBO J.*, 2(12):2143–2150 (1983).

*Primary Examiner*—Douglas W. Robinson
*Assistant Examiner*—Elizabeth F. McElwain
*Attorney, Agent, or Firm*—Marshall, O'Toole, Gerstein, Murray & Borun

[57] ABSTRACT

Provided are transgenic plants with resistance to viral infection, methods for conferring such resistance, and methods for producing the transgenic plants.

5 Claims, 1 Drawing Sheet

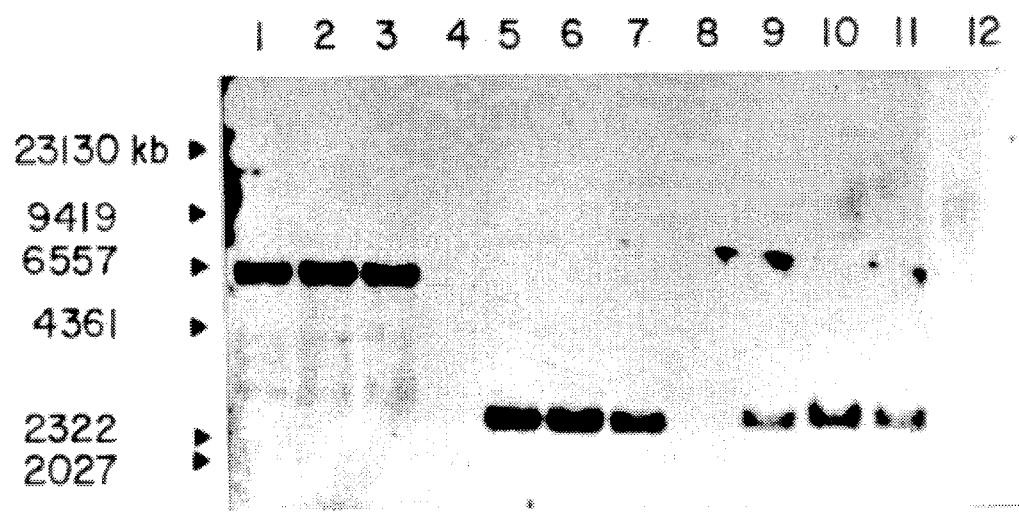

VIRUS-RESISTANT TRANSGENIC PLANTS

FIELD OF THE INVENTION

The present invention generally relates to materials and methods for conferring resistance to viral infection in plants. More specifically, the invention relates to transgenic plants and methods of their preparation, wherein said plants are resistant to infection by viruses.

BACKGROUND OF THE INVENTION

Plant pathogens have a profound impact on agricultural production. Accordingly, the control and eradication of certain plant viruses is of economic importance. One plant pathogen of economic interest is the potato virus Y. That virus is a member of the polyviridae family, the largest known group of plant viruses. Potato virus Y infects and causes damages in several plant species, including members of the Solanaceae family. In one member of that family, comprising species of potato, infection by potato virus Y may result in as high as an 80% reduction in crop yield. However, despite its name, potato virus Y is pathogenic in a variety of plant species, including non-potato species.

Of interest to the present invention is the P1 gene of potato virus Y. That gene encodes one of eight functional proteins produced by processing of a primary polyprotein encoded by the 9.7 Kb genome of potato virus Y. Protein P1 is encoded near the 5' end of the viral genome and is a 35 kDa protein having C-terminal proteolytic activity. The P1 protein has also been reported to bind RNA. Brantley, et al., J. Gen. Virol., 74:1157–1162 (1993).

Also of interest to the present invention are reports that genetically-engineered pathogen-derived resistance to viral pathogens has been achieved in several plant species. For example, resistance to viral infection has been reported in plants transformed with viral coat protein-encoding genes. Hull, et al., Grit. Rev. Plant Sci., 11: 17–33 (1992). Recently, there have been several reports that resistance to a plant virus may be achieved by transforming a susceptible plant with non-structural genes of the virus. However, such attempts have produced relatively strain-specific resistance. For example, strain-specific viral resistance has been reported by transformation of a strain of tobacco with replicase genes of tobacco mosaic virus. Longstaff, et al., EMBO J., 12:379–386 (1993). Similar strain-specific result in tobacco have been reported by transformation with potato virus Y. Audy, et al., 12 Annual Meeting of the American Society of Virology, University of California at Davis, Calif. 7 (1993). Finally, strain-specific resistance to potato virus Y infection has been reported in tobacco having been transformed with the NIa proteinase of potato virus Y.

To date, methods for introduction of viral resistance in plants, and especially methods for achieving resistance to potato virus Y and other economically-important viruses, have been relatively strain-specific. Moreover, there are no reports of the use of P1 to generate resistance to any virus in potatoes or any other species. Accordingly, there is a need in the art for a method for conferring resistance to viral pathogen across a range of species. In addition, due to the economic importance of controlling plant pathogens, and especially plant pathogens infecting food crops, there is a need in the art for additional transgenic virus-resistant species and methods for making such transgenic species.

SUMMARY OF THE INVENTION

The present invention generally relates to transgenic plant species having resistance to infection by one or more viral plant pathogens, to methods for conferring such resistance, and to methods for producing said transgenic plant species. Unlike materials and methods reported in the art, transformation of plant species as taught herein confers resistance to various viruses on a wide range of different plant species and wherein a gene, the P1 gene, is used in a manner not previously reported.

Transgenic plants and methods for making and using them according to the present invention are useful to increase the viability of plant crops and to increase plant yields. Transgenic plants and methods for producing them according to the present invention reduce crop loss due to infection by viral pathogens.

In general, the present invention provides transgenic plants resistant to infection by a virus selected from the group consisting of potato virus Y, potato leaf roll virus, potato virus A, potato virus V, potato moptop virus, potato yellow dwarf virus, tobacco mosaic virus, tobacco etch virus, tobacco vein molting virus, tobacco ringspot virus, tobacco streak virus, tobacco yellow dwarf virus, tomato golden mosaic virus, tomato spotted wilt virus, tomato bushy stunt virus, tomato ring spot virus, tomato black ring virus, pepper ringspot virus, pepper mottle virus, pepper mild mottle virus, and pepper veinal mottle virus (collectively refereed to as "the viruses). Plant species in which resistance may be conferred include potatoes, tomatoes, tobacco, peppers, cabbage, pine, spruce, maize, wheat, rice, and birch. Generally, the resistance conferred by methods and materials according to the present invention is effective against any virus in the Potyviridae family and other phyla. Plant species capable of being infected by the viruses mentioned above are rendered resistant to one or more of the viruses upon transformation according to the methods taught herein.

In a preferred embodiment of the invention, a plant species capable of being infected by one or more of the viruses is genetically transformed with DNA encoding a P1 protein of potato virus Y or an effective portion thereof. As used herein, an effective portion of a P1 protein of potato virus Y is a portion of that protein which retains a proteolytic activity as characterized, inter alia,.in Verchot, et al., Virology, 185:527–535 (1991) and/or which retains RNA binding activity characteristic of P1. Also in a preferred embodiment of the invention, a plant capable of being pathogenically infected by one or more of the viruses is transformed with a vector comprising DNA encoding a P1 protein or an effective portion thereof. P1 vector DNA may be further transformed into a plasmid, such as a Ti-plasmid, for further transformation into a plant. However, the skilled artisan is aware of various means for transforming plants. Transgenic plant species according to the invention preferably may be transformed with DNA as shown in SEQ ID NO: 3. Suitable plants for transformation as described herein include, but are not limited to, those mentioned above. Viruses against which resistance may be conferred according to the present invention include, but are not limited to, the viruses mentioned above.

Also in a preferred embodiment of the invention, a transgenic potato is taught which has resistance to infection by potato virus Y. A transgenic potato according to the present invention may be a potato having been transformed with DNA encoding a P1 protein of potato virus Y or an effective portion thereof. A transgenic potato according to the present invention may be a potato having been transformed with DNA as shown in SEQ ID NO: 3. Also in a preferred embodiment, a potato shoot may be transformed with DNA encoding a P1 protein of potato virus Y.

In a method according to the present invention, transgenic plants are produced by transforming plantlets with DNA comprising a P1-encoding portion. The skilled artisan appreciates that any plant cell may be transformed by methods described herein. However, it is preferred to conduct transformation in plantlets (i.e., cultivars approximately four weeks old). In a preferred embodiment, P1-encoding DNA is transformed as part of a vector and may preferably be part of a plasmid, such as pHTT294, further conjugated into a Ti plasmid of *Agrobacterium tumefaciens*, which is then transformed into plant cells. Also in a preferred embodiment, the transgenic plant may be selected from the group consisting of tuber crops and, further from the group consisting of potatoes, cauliflower, tobacco, tomatoes, and carrots.

Also provided by the present invention are methods for production of transgenic plants having a resistance to potato virus Y, comprising the steps of transforming a plant with DNA encoding P1 or an effective portion thereof and cultivating the resulting transformants under normal growth conditions.

DNA comprising a region encoding an effective portion of P1 protein of potato virus Y is effective in conferring resistance to viral infection in numerous species and strains of plants. Specifically, the P1 protein of potato virus Y is useful for conferring resistance to numerous viruses which infect members of the Solanaceae family and other plant families, including potato, tobacco, and pepper species, as well as members of related families, as listed above. Accordingly, while the present invention is specifically exemplified by conferring resistance to potato virus Y infection in potatoes, the invention may also be applied to confer resistance to other viruses in other plant species as enumerated above using P1. In addition, the invention may be used to confer resistance to other viruses in potatoes. Accordingly, application of the present technology to species not specifically exemplified herein is expected to function to confer resistance to such species. Additional aspects and advantages of the present invention will become apparent to the skilled artisan upon consideration of the following detailed description thereof.

DESCRIPTION OF THE DRAWING

FIG. 1 represents Southern blots of HindIII (lanes 1–4); SmaI plus HindIII (lanes 5–8); and SmaI (lanes 9–12) digests of DNA from PVY-resistant and PVY-susceptible P1 transgenic PITO plants.

DETAILED DESCRIPTION OF THE INVENTION

The present invention provides a new strategy for generating resistance against a variety of plant viruses by transformation of susceptible plants with a P1 gene of potato virus Y. The results provided below establish a high resistance to infection in transformed plants. The following Examples are illustrative of the invention and provide preferred embodiments thereof. However, it is apparent to the skilled artisan that various embodiments of the invention not provided herein will also achieve the result of conferring resistance upon transformed plant cells.

EXAMPLE 1

EXTRACTION OF VIRAL RNA AND SYNTHESIS OF cDNA

Numerous methods for the extraction and purification of RNA and manufacture of cDNA libraries are known. See, e.g., Sambrook, et al., Molecular cloning: A Laboratory Manual, 7.3–7.84 and 8.3–8.82 (1989). Consequently, any known method may be used to generate cDNA encoding a P1 protein of potato virus Y for use according to the methods taught herein.

In order to generate potato virus Y (PVY) cDNA, tobacco leaves were infected with a wild-type strain of PVY. Such a strain is reported in Gibson, et al., Ann. Appl. Biol., 116:151–156 (1990), incorporated by reference herein. A crude viral extract was prepared according to the method of Edwards, et al., Nucl. Acids Res., 19:1349 (1991), incorporated by reference herein, in order isolate total viral RNA. To extract RNA, leaf tissue was frozen in liquid nitrogen and was then ground to a fine powder. An equal volume of extraction buffer (200 mM Tris-Hcl, pH 7.5, 250 mM NaCl, 25 mM EDTA, 0.5% SDS) was then added, mixed well, and the extracts were vortexed for 5 seconds. Extracts were then centrifuged at 13,000 rpm for 1 minute and 300 µl of the supernatant were transferred to a fresh tube. That tube was left at room temperature for about two minutes with the addition of 300 µl isopropanol. The extract was then centrifuged at 13,000 rpm for 5 minutes and the pellet was vacuum dried and dissolved in 100 µl TE (10 mM Tris, pH 8.0; 1.0 mM EDTA).

The RNA preparation obtained was used in the preparation of a cDNA library using a 1st Strand Synthesis Kit (Pharmacia) according to the manufacturer's instruction. A random hexanucleotide mixture was used to prime the RNA.

The cDNA obtained as provided above was subjected to PCR amplification using a Taq DNA polymerase (Promega). The upstream primer for amplification was 5'GGGAAT-TCATATGGCAACTTACATGTCAACA 3' (SEQ ID NO: 1), which corresponds to nucleotides 185 through 205 of the PVY$^n$ (the similarity of the sequences of PVY$^n$ and PVY$^o$ allows the use of either strain for construction of PCR primers) RNA sequence [Robaglia et al., J. Gen. Virol., 70:935–947 (1989)] with additional EcoRI and NdeI sites. The downstream primer was 3' GGGGATCCACTCTGAG-TAACTCTAGAACGTGC 5' (SEQ ID NO: 2), corresponding to nucleotides 989 through 1012 of the PVY$^n$ RNA sequence with an additional BamHI site. The amplified region corresponds to the P1 gene. PCR was carried out using a PTC-100 Thermocycler with a programmable Thermal Controller (MJ Research) at 92-35-72° C. for 30 cycles. The skilled artisan knows standard PCR protocols. See, e.g., Ausubel, et al., Current Protocols in Molecular Biology: §15 (1989).

The resulting PCR product is shown in SEQ ID NO: 3. That product was cloned into a pCR1000 cloning vector obtained from the TA Cloning System (Invitrogen) according to the manufacturer's instructions. The cloned fragment was also subcloned into a pET3a expression vector (Novagen) by ligating the NdeI and BamHI digested fragment into unique NdeI and BamHI sites in the vector. The nucleotide sequence of the cloned fragment was obtained by the dideoxy chain termination method of Sanger, Proc. Nat'l. Acad. Sci. (USA), 74:5463–5467, using an AutoRead DNA Sequencer Kit and an A.L.F. Automated DNA Sequencer (Pharmacia Biotech).

EXAMPLE 2

CLONING AND SEQUENCE ANALYSES

The cloning procedure described above resulted in the production of a cDNA clone containing the entire 31 kDa open reading frame of P1. The nucleotide sequence of the cloned fragment (SEQ ID NO: 3) was confirmed to correspond to a previously published P1 sequence of PVY$^o$ (GenBank Accession No. M37180, reported in Thornbury et al., Virology 178:573–578 (1990)) with 94.6% homology at the nucleotide level corresponding to 97% homology at the amino acid level. The translation integrity of the cloned sequence was confirmed by in vitro translation of the cloned sequence in rabbit reticulocyte lysate, which resulted in the production of a 31 kDa product as predicted from the amino acid sequence of the native protein.

EXAMPLE 3

The cloned P1 sequence described in Example 1 was inserted into unique BamHI sites in a pHTT294 plasmid (pHTT294P1S) in sense orientation. The pHTT294 plasmid (pHTT294P1S) containing the cloned P1 sequence was deposited with the American Type Culture Collection, 12301 Parklawn Drive, Rockville, Md. 20852, on Apr. 1, 1994 as accession number ATCC 75726. Correct orientation was confirmed by restriction fragment analysis. That plasmid was then further conjugated into an *Agrobacterium tumefaciens* (C58C1, Van Larebece, et al., Nature, 252:169–170 (1974)) Ti-plasmid (pGV3850, Zambryski, et al., EMBO J., 12:2143–2150 (1983) by triparental mating using a GJ23 helper plasmid described in Van Haute, et al., EMBO J., 12:411–417 (1983). The construct contained a kanamycin-resistance gene. Portions of stems (approximately 3–5 mm each) were excised from 4-week-old plantlets of potato cultivar PITO, a commercially-available variety of potato produced in Finland, and were transformed with the above-described Ti-plasmid. Explants were grown on MS medium (4.71 g/L MS salts; 30 g/L sucrose, 6.0 g/L agar, pH 5.2), as reported in Murashige, et al., Physiologia Plantarum, 15:473–497, incorporated by reference herein, supplemented with 2.25 mg/L BAP (6-bentsylaminopurine), 0.2 mg/L NAA (α-napthaleneacetic acid), and 0.1 mM acetosyringone for 48 hours prior to inoculation with Agrobacterium.

An overnight culture of *A. tumefaciens* grown in liquid LB medium was diluted 1:10 with liquid MS medium and explants were immersed in the inoculum. Explants were then dried briefly against a sterile filter paper and incubated on MS plates at pH 5.8 with BAP and NAA for 48 hours under shaded light at 28° C. in a growth chamber. Explants were next washed with 500 mg/L cefotaxime and placed on fresh MS medium containing cefotaxime in the same concentration as in the wash. Ten days later, explants were transferred onto MS medium (pH 5.8) containing 75 mg/L kanamycin and grown for 7 days. Finally, the explants were transferred onto MS medium (pH 5.8) supplemented with 2.25 mg/L BAP, 35.0 mg/L giberillic acid and 75 mg/L kanamycin. Shoots regenerated approximately 28–35 days after agroinfection.

EXAMPLE 4

INOCULATION OF TRANSGENIC PLANTS WITH PVY

In vitro-derived potato plants were transplanted into soil and grown in a greenhouse under natural daylight extended and supplemented by fluorescent illumination with a photoperiod of 18 hours. Daily mean minimum temperature was 23° C. and daily mean maximum temperature was 27° C. Sap was extracted from the uppermost fully-expanded leaves of PVY$^o$-infected *Nicotiana tabacum* L. cv. Samsun, diluted 1:3 with distilled water, and rubbed onto carborundum-dusted leaves of 6-week-old potato plants. Three plants of each of the P1-transgenic lines were inoculated. Non-transformed plants of PITO were included as controls.

Two uppermost fully-expanded leaves were tested for PVY 14 and 21 days after inoculation using the direct double antibody sandwich enzyme-linked immunosorbent assay (DAS-ELISA) using p-nitrophenyl as substrate. Absorbencies were recorded at 405 nm using an ELISA reader (Titertek Multiscan). Serial dilutions of purified PVY$^o$ was used as a standard in ELISA tests.

EXAMPLE 5

SCREENING OF TRANSGENIC PLANTS

Samples of leaf tissue (30–40 mg) from plants regenerated on a kanamycin-containing selection medium were screened for expression of the NPTII protein using the method of McDonnell, et al., Plant Mol. Biol. Rep., 5:380–386 (1987), incorporated by reference herein. The NPTII protein is neomycin phosphotransferase II which confers kanamycin resistance. Leaf tissue (30–40 mg) was ground in an Eppendorf tube, to which 30–40 µl extraction buffer (20% glycerol, 125 mM Tris-Hcl, pH 6.8, 10% β-mercaptoethanol, 0.2% SDS) was added. After grinding, tubes were vortexed for 10 seconds and placed on ice. The tubes were then centrifuged for 10 minutes at 15,600×g at room temperature and the resulting supernatant was transferred to a new tube. In an Eppendorf tube, 5 µl of each sample extract and 5 µl of an assay mixture (0.03 mM kanamycin, 1.48 mM ATP, 18 mM NaF, 10 µCi gamma-32-labelled phosphorus) were mixed and incubated for 20 minutes at 37° C. Samples were then centrifuged briefly and 5 µl of each sample was spotted onto a dried Whatman™ P81 (cellulose phosphate) paper which had been soaked in a solution of 20 mM ATP and 100 mM pyrophosphatase. After the spots had dried, the paper was washed for 2 minutes in 10 mM sodium phosphate buffer at pH 7.5 and 80° C. The blots were then washed in 10 mM sodium buffer at room temperature for 10 minutes, a step which was repeated 3–5 times. Finally, the blots were dried and exposed to x-ray film for 16 to 48 hours.

Genomic DNA was then isolated from leaf tissue of the transformants and control plants using the procedure of Dellaporta, et al., Plant Mol. Biol., 15:39–47 (1983), incorporated by reference herein, including phenol-chloroform and CTAB extractions. Specifically, isolation of genomic DNA was accomplished by weighing 2–4 g potato leaves, which were then ground in liquid nitrogen to a fine powder using a mortar and pestle. The powder was then transferred to a 50 ml centrifuge tube containing 20 ml extraction buffer (500 mM NaCl, 100 mM Tris-HCl, pH 8.0, 50 mM EDTA). An aliquot of 2.7 ml of 10% SDS was then added and the tube was shaken and incubated at 65° C. for +minutes. A ⅓ volume of 5 M potassium acetate was then added and mixed well. The tube was then placed on ice for 30 minutes, after which it was centrifuged at 20,000×g for 15 minutes at 4° C. The supernatant was then poured through cheesecloth and a 0.7 volume of isopropanol was added. The tube was then placed on ice for 30 minutes and subsequently centrifuged at 1000×g for 10 minutes. The pellet was dissolved in 2 ml TE overnight at 4° C. The pellet was then incubated at 37° C. for 30 minutes upon addition of 4 µl RNAase. Phenol-chloroform extraction was then performed (2–4 times) followed by CTAB extraction (1% CTAB, 1.25 M NaCl, incubated 10 minutes at 60° C.), followed by two chloroform extractions.

Two volumes of ethanol were then added and the tube was placed on ice for 15 minutes. Finally, the tube was centrifuged at 3000×g for 10 minutes, the resulting pellet was washed with 75% ethanol and then dried in a Speed Vac and dissolved in 250 μl to 500 μl TE buffer.

The cloned P1 sequence was radioactively labeled with $\alpha^{32}P$ CTP according to the instructions of the manufacturer (Oligolabelling Kit, Pharmacia) and was used to probe HindIII, HindII plus SmaI, and SmaI digested DNA samples.

EXAMPLE 6

ANALYSIS OF TRANSGENIC PLANTS

Randomly-selected transformants, regenerated on medium (MS medium supplemented with 2.25 mg/L BAP, 35.0 mg/L gibberillic acid) containing kanamycin (75 mg/L), were allowed to root on a kanamycin-free medium. Seventy one of the rooted $R^0$ plantlets were assayed for neomycin phosphotransferase activity (NPTII) by methods described in McDonnell et al., supra. Thirty five of the tested seedlings were NPTII positive and represented 27 independent cell lines. Growth and appearance of the NPTII positive plants was similar to those of non-transformed control plants of Pito.

Nine of the NPTII positive $R_0$ plants were assayed for viral resistance by ELISA. The results are summarized in Table 1; wherein mean $PVY^o$ concentrations (μg $PVY^o$/g potato leaves) in each of the three copies (a,b,c) of P1 transgenic lines, and in untransformed PITO control (inoculated and uninoculated) were measured 14 and 21 days post inoculation (dpi). In all ELISA experiments, serial dilutions of purified $PVY^o$ was used as standards.

TABLE 1

| | | PVY° (μg/g leaves) | |
|---|---|---|---|
| Cell Line | | 14 dpi | 21 dpi |
| Experiment 1: | | | |
| 1002SI1 | a | 0,0 | ND |
| | b | 0,0 | ND |
| | c | 0,0 | ND |
| SI0319-1 | a | 561,0 | ND |
| | b | 510,0 | ND |
| | c | 1122,0 | ND |
| PITO control (inoculated) | a | 244,8 | ND |
| | b | 142,8 | ND |
| PITO control (uninoculated) | a | 0,0 | ND |
| | b | 0,0 | ND |
| Experiment 2: | | | |
| SI0626-1 | a | 112,2 | 127,5 |
| | b | 260,1 | 89,4 |
| | c | 484,5 | 255,0 |
| SI0319-3 | a | 237,0 | ND |
| | b | 99,0 | ND |
| | c | 330,0 | ND |
| SI0605-1 | a | 0,0 | ND |
| | b | 264,0 | ND |
| | c | 114,0 | ND |
| PITO control (inoculated) | a | 210,0 | 107,1 |
| | b | 109,8 | 188,7 |
| PITO control (uninoculated) | a | 0,0 | 0,0 |
| | b | 0,0 | 0,0 |
| Experiment 3: | | | |
| SI0601-2 | a | 0,0 | 64,8 |
| | b | ND | 0,0 |
| | c | 76,5 | 54,0 |
| SI0305-1 | a | 0,0 | 0,0 |
| | b | 0,0 | 0,0 |
| | c | 0,0 | 0,0 |
| SIII1113-1 | a | 0,0 | 0,0 |
| | b | 0,0 | 0,0 |
| | c | 0,0 | 0,0 |
| SI0523-1 | a | ND | 0,0 |
| | b | ND | 18,3 |
| | c | ND | 17,7 |
| PITO control (inoculated) | a | 45,9 | 125,4 |
| | b | 178,9 | 57,0 |
| PITO control (uninoculated) | a | 0,0 | 0,0 |
| | b | 0,0 | 0,0 |

ND = not determined

As shown in Table 1, no PVY was detected in the P1-transformants, 1002SI1, SIII 1113-1 and SI0305-1, representing three independent lines, 21 days after inoculation. Those plants also remained symptomless. In contrast, other tested lines transformed with P1 showed mosaic symptoms and had high PVY titres similar to those of nontransformed PVY-infected Pito plants. Two of the NPTII positive $R_0$ plants, one resistant plant, 1002SI1, and one susceptible plant, S10319-1, were analyzed by Southern blot hybridization using the cloned P1 sequence as a probe. Southern analysis confirmed the presence of the transgene in the genome of the resistant plant as a single insert, but no signal was detected in Southern analysis of the susceptible plant. The results are shown in FIG. 1; wherein lanes 1–3, 5–7, and 9–11 are blots from three different copies of a resistant strain; and lanes 4, 8, and 12 are blots from a susceptible strain.

We claim:

1. A potato plant transformed with DNA encoding a P1 protein of potato virus Y or a portion thereof which retains P1 proteolytic activity and which binds RNA.

2. The potato according to claim 1, wherein said P1 sequence is shown in SEQ ID NO: 3.

3. A potato plant shoot transformed with a vector comprising a P1 DNA of potato virus Y or a portion thereof which retains P1 proteolytic activity and which binds RNA.

4. A method for conferring resistance to potato virus Y in a potato species, comprising the step of:

transforming one or more members of said potato species with DNA encoding a P1 protein of potato virus Y.

5. A method for production of potato plants having resistance to potato virus Y, comprising the steps of:

a) transforming a potato plant or a potato plant shoot with a P1 DNA of potato virus Y; and b) cultivating said potato plant or potato plant shoot.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear -continued ( i i ) MOLECULE TYPE: cDNA ( x i ) SEQUENCE DESCRIPTION: SEQ ID NO:1:

```
GGGAATTCAT ATGGCAACTT ACATGTCAAC A                                31
```

( 2 ) INFORMATION FOR SEQ ID NO:2:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

```
CGTGCAAGAT CTCAATGAGT CTCACCTAGG GG                               32
```

( 2 ) INFORMATION FOR SEQ ID NO:3:

( i ) SEQUENCE CHARACTERISTICS:
( A ) LENGTH: 828 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

```
ATGGCAACTT ACATGTCAAC AATCTGTTTC GGTTCGTTTG AATGCAAGCT ACCATACTCA    60
CCCGCCTCTT GCGGGCATAT TGCGAAGGAA CGAGAAGTGC TGGCTTCCGT TGATCCTTTT   120
GCAGATCTGG AAACACAACT TAGTGCACGA TTGCTCAAGC AAGAATATGC TACTGTTCGT   180
GTGCTCAAGA ACGGTACTCT TACGTACCGA TACAAGACTG ATGCCCAGAT AACGCGCATC   240
CAGAAGAAAC TGGAAAGGAA GGATAGGGAA GAATATCACT TCCAGATGGC AGCTCCTAGT   300
ATTGTGTCAA AAATTACTAT AGCTGGTGGA GATCCTCCAT CAAAGTCTGA GCCACAAGCA   360
CCAAGAGGTA TCATTCATAC AACTCCAAGG GTGCGTAAAG TCAAGACACG CCCCATAATA   420
AAGTTGACAG AACCGGAGAT GGATCATCTC ATTAAGCAGG TGAAGCAGAT TATGTCGGGG   480
AAGAGAGGGT CTGTTCACTT AATTAGTAGA AAGACCACCC ATGTTCAATA TAAGGAGATA   540
CTTGGTGCAA CTCGCGCAGC GGTTCGAACT GCACATATGC TGGGCTTGCG ACGGAGAGTG   600
GACTTCCGAT GTGATATGTG GACAGTTGGA CTTTTGCAAC GTCTCGCTCG GACGGACAAA   660
TGGTCCAATC AAGTCCGCAC TATCAACATA CGAAAGGGTG ATAGTGGAGT CATCTTGAAC   720
ACAAAAAGTC TCAAAGGCCA CTTTGGTAGA AGTTCAGGAG ACTTGTTCAT AGTGCGTGGA   780
TCACACGAAG GGAAATTGTA CGATACACGT TCTAGAGTTA CTCAGAGT                828
```